(12) United States Patent
Deshays

(10) Patent No.: US 8,313,017 B2
(45) Date of Patent: Nov. 20, 2012

(54) SEALED ENCLOSURE FOR THE DECONTAMINATION OF A MEDICAL APPARATUS

(75) Inventor: Clement Deshays, Ruoms (FR)

(73) Assignee: Germitec, Clichy (FR)

( * ) Notice: Subject to any disclaimer, the term of this patent is extended or adjusted under 35 U.S.C. 154(b) by 411 days.

(21) Appl. No.: 12/594,153

(22) PCT Filed: Apr. 16, 2008

(86) PCT No.: PCT/FR2008/000540
§ 371 (c)(1),
(2), (4) Date: Oct. 15, 2009

(87) PCT Pub. No.: WO2008/142299
PCT Pub. Date: Nov. 27, 2008

(65) Prior Publication Data
US 2010/0140134 A1 Jun. 10, 2010

(30) Foreign Application Priority Data
Apr. 18, 2007 (FR) ...................... 07 54546

(51) Int. Cl.
*G06F 17/00* (2006.01)
(52) U.S. Cl. ........................ 235/375; 235/383
(58) Field of Classification Search .................. 422/292; 235/375, 376, 380, 381, 383, 385
See application file for complete search history.

(56) References Cited

U.S. PATENT DOCUMENTS

| | | |
|---|---|---|
| 4,772,795 A | 9/1988 | Sakurai et al. |
| 5,185,532 A | 2/1993 | Zabsky et al. |
| 5,310,524 A | 5/1994 | Campbell et al. |
| 5,610,811 A | 3/1997 | Honda |
| 5,641,464 A | 6/1997 | Briggs, III et al. |
| 5,690,113 A | 11/1997 | Sliwa, Jr. et al. |
| 5,761,069 A | 6/1998 | Weber et al. |
| 6,039,928 A | 3/2000 | Roberts |
| 6,171,559 B1 | 1/2001 | Sanders et al. |
| 6,231,819 B1 | 5/2001 | Morello |
| 6,260,560 B1 | 7/2001 | Walta |
| 6,475,433 B2 | 11/2002 | McGeorge et al. |
| 6,485,979 B1 | 11/2002 | Kippenhan et al. |
| 6,641,781 B2 | 11/2003 | Walta |

(Continued)

FOREIGN PATENT DOCUMENTS

DE 3209701 A1 9/1983

(Continued)

OTHER PUBLICATIONS

International Search Report for PCT/FR2008/000540, mailing date of Jan. 22, 2009.

(Continued)

*Primary Examiner* — Sean E Conley
(74) *Attorney, Agent, or Firm* — Morrison & Foerster LLP

(57) ABSTRACT

The invention relates to an enclosure of the type including a base (6), at least one side wall (7) and an upper lid (8) defining a decontamination volume (9), wherein one of said side walls (7) comprises an access opening (10) to the decontamination volume (9) extending up to the upper lid (8), the upper lid (8) including a cable passage (12) open towards said opening and a cable suspension member (14) through said cable passage. The enclosure includes a blocking flap (13) movable between a cable passage (12) closing position in which the flap (13) tightly closes the cable passage (12), and a cable passage (12) opening position.

11 Claims, 6 Drawing Sheets

U.S. PATENT DOCUMENTS

| | | |
|---|---|---|
| 7,965,185 B2 | 6/2011 | Cambre et al. |
| 2001/0024623 A1 | 9/2001 | Grimm et al. |
| 2002/0162972 A1 | 11/2002 | Pleet |
| 2003/0016122 A1 | 1/2003 | Petrick |
| 2003/0039579 A1 | 2/2003 | Lambert et al. |
| 2003/0187586 A1 | 10/2003 | Katzenmaier et al. |
| 2004/0009091 A1 | 1/2004 | Deal et al. |
| 2004/0140347 A1 | 7/2004 | Mihaylov et al. |
| 2004/0209223 A1 | 10/2004 | Beier et al. |
| 2005/0196314 A1 | 9/2005 | Petersen et al. |
| 2008/0213139 A1 | 9/2008 | Deshays |
| 2008/0219899 A1 | 9/2008 | Deshays |
| 2009/0169436 A1 | 7/2009 | Deshays |
| 2010/0140342 A1 | 6/2010 | Deshays |

FOREIGN PATENT DOCUMENTS

| | | |
|---|---|---|
| DE | 3917876 A1 | 12/1990 |
| DE | 19703823 C1 | 5/1998 |
| DE | 19917206 A1 | 10/2000 |
| DE | 10225232 A1 | 12/2002 |
| DE | 10225857 A1 | 1/2004 |
| EP | 0 471 530 A1 | 2/1992 |
| EP | 0 630 820 A1 | 12/1994 |
| EP | 0 630 820 B1 | 12/1994 |
| EP | 0 709 056 A1 | 5/1996 |
| EP | 0 709 056 B1 | 5/1996 |
| EP | 0839537 A1 | 5/1998 |
| EP | 1 402 904 A1 | 3/2004 |
| EP | 1 532 989 A1 | 5/2005 |
| FR | 2753905 A1 | 4/1998 |
| FR | 2890566 A1 | 3/2007 |
| FR | 2890865 A1 | 3/2007 |
| WO | WO-84/00009 A1 | 1/1984 |
| WO | WO-99/08137 A1 | 2/1999 |
| WO | WO-2004/111917 A1 | 12/2004 |
| WO | 2005/048041 A2 | 5/2005 |

OTHER PUBLICATIONS

International Search Report mailed on Jan. 22, 2009, for PCT Application No. PCT/FR2008/000541, 3 pages.

International Search Report mailed on Sep. 11, 2007, for PCT Application No. PCT/FR2007/000594, 3 pages.

International Search Report mailed on Jul. 6, 2006, for PCT Application No. PCT/FR2005/003032, 3 pages.

International Search Report mailed on Mar. 21, 2006 for PCT Application No. PCT/FR2005/003031, 3 pages.

SEALED ENCLOSURE FOR THE DECONTAMINATION OF A MEDICAL APPARATUS

The invention relates to an enclosure of the type that comprises a base, at least one side wall, and a top cover, which delimit a decontamination space, wherein one of said at least one side walls comprises an opening extending to the top cover for access to the decontamination space, and the top cover comprises a cable passage that opens into said opening and a member for suspending a cable through said cable passage.

Enclosures of this type are known, and are used for disinfecting the active part of a medical probe intended for use with an imaging device, for example.

Disinfection can be done using UV radiation, by atomizing a liquid disinfectant in the form of micro-droplets, or by injecting a gas disinfectant into the decontamination space of the enclosure, for example.

In such an enclosure, the active part of the probe must be suspended in the decontamination space in order to obtain the largest possible disinfection surface. In addition, the cable that joins the active part of the probe to the device with which the probe is used should preferably not be put entirely inside the enclosure, in order to protect the part of this cable that connects to the imaging device, and to optionally allow the probe not to be disconnected from the imaging device while it is being disinfected.

Such an implementation thus requires the provision of a cable passage allowing the active part of the probe to be placed in the enclosure and part of the cable to be left outside said enclosure. This raises an issue of sealing the decontamination enclosure, since the active principle can get out of the enclosure through the cable passage.

One of the purposes of the invention is to propose a decontamination enclosure in which the enclosure can be tightly sealed when the probe is set therein.

To this end, the invention relates to a decontamination enclosure of the aforementioned type, characterized in that it comprises a flap seal that is movable between a closed position of the cable passage, in which the flap closes the cable passage hermetically, and an open position of the cable passage.

The flap for closing the cable passage makes it possible to ensure that the enclosure is perfectly sealed when it is shut, even though the probe cable extends outside of it.

According to other characteristics of the decontamination enclosure of the invention:
- the cable passage comprises a slot provided in the top cover;
- the flap is borne by the cover;
- the enclosure comprises a door for closing the access opening to the decontamination space, with said door arranged so that closing it brings the mobile flap toward a position where it closes off the cable passage;
- the flap is integral with the top part of the door and is arranged so as to close the cable passage hermetically when the door is closed;
- the cable suspension member comprises a clamp;
- the cable suspension member comprises a hook;
- the cable suspension member comprises an open tube that is hermetically fittable over a portion of the medical instrument cable, whose diameter is within a range of predetermined diameters;
- the suspension member comprises a part for receiving a suspension part provided on the cable of the medical instrument, wherein said receiving part and said suspension part form a fastening assembly comprised of a male part and a female part;
- the enclosure comprises means for reading an electronic identification label provided on a cable of the medical instrument, with said label being placed near the active part of the medical instrument to be disinfected, and said reading means being arranged so as to be near the identification label when the cable is suspended on the cable suspension member; and
- the means for reading an electronic identification label comprise a short-range RFID reader.

Other aspects and advantages of the invention will appear in the following description, given as an example and with reference to the annexed figures.

Figure 1:
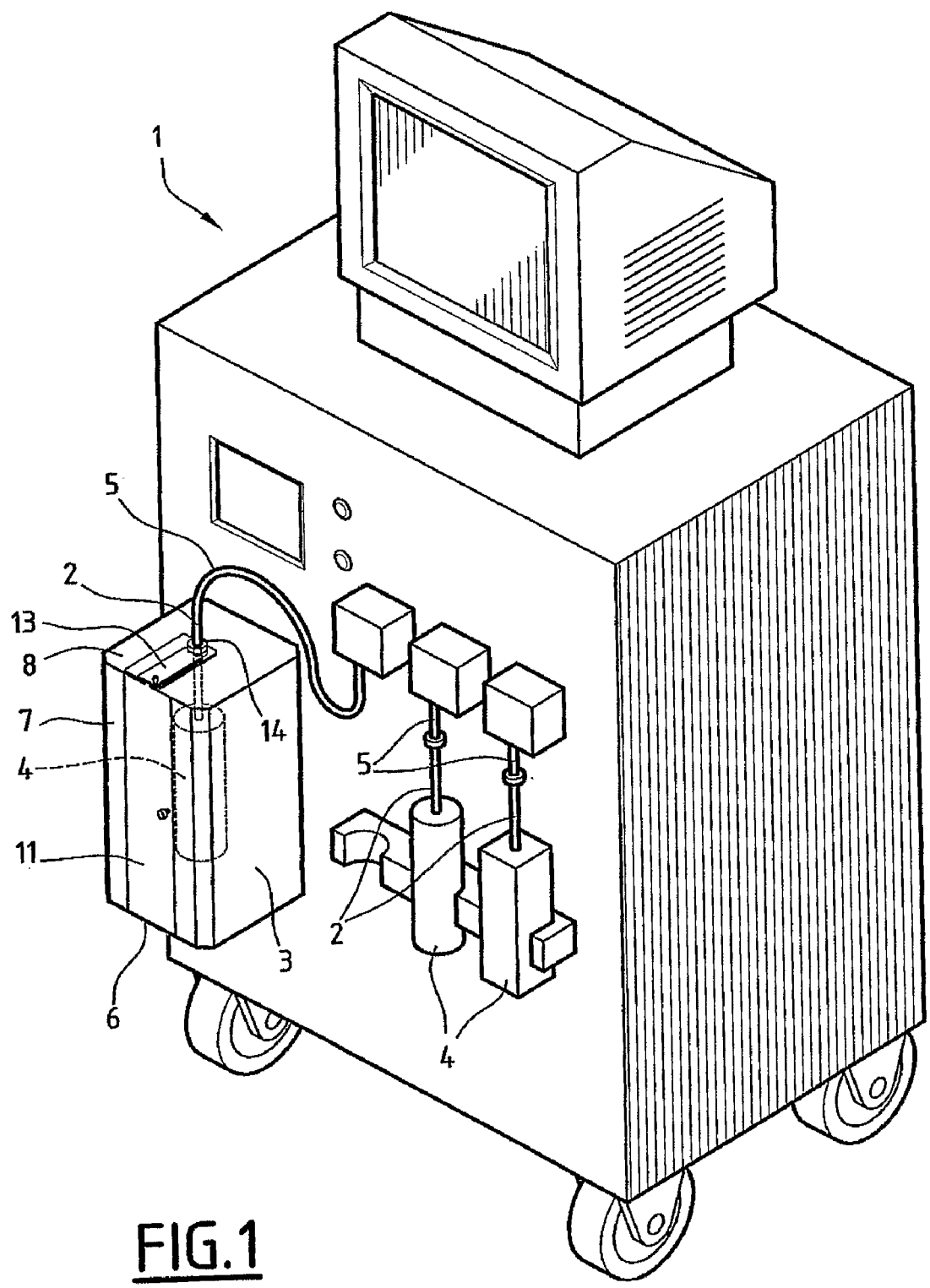
FIG. 1 is a schematic perspective view of a medical imaging device to which a decontamination enclosure according to the invention is attached, with a probe placed in the enclosure.

With reference to FIG. 1, we will describe a medical imaging device 1 that is operable with a plurality of probes 2 and to which an enclosure 3 is attached for decontaminating the active parts 4 of the probes 2.

In the embodiment shown in the figures, the decontamination enclosure 3 is attached to the imaging device 1. According to other embodiments, the enclosure 3 is independent of the imaging device 1 or is attached to another medical apparatus.

In the embodiment shown in the figures, three probes 2 are connected to the imaging device 1. According to other embodiments, a different number of probes can be provided. The imaging device 1 is known in itself and will not be described in more detail here. A probe 2 comprises an active part 4 that must be disinfected before each use and a cable 5 for connecting to the medical apparatus 1, the connecting part of which must not be exposed to the active principle used in the disinfection process. The probe 2 is known in itself and will not be described in more detail here.

The enclosure 3 comprises a base 6 forming the bottom of the enclosure, at least one side wall 7 forming the body of the enclosure, and a top cover 8. The side wall 7 extends between the base 6 and the top cover so as to delimit a decontamination space 9 in which the active part 4 of the probe 2 is placed in order to be disinfected.

According to the embodiment shown in the figures, the enclosure 3 is substantially parallelepipedic and comprises four side walls 7. According to other embodiments, the enclosure 3 can be substantially cylindrical with circular section or otherwise.

The enclosure 3 comprises means (not shown) for diffusing a disinfectant active principle in the decontamination space 9. These means are, for example, a source of UV emission, a micro-droplet spray nozzle for a liquid disinfectant, or an injection nozzle for a gas disinfectant. The diffusion means are arranged so that the active part 4 of the probe 2 is uniformly exposed to the disinfectant active principle.

In the embodiment shown in the figures, the wall 7 opposite the imaging device comprises an opening 10 that can be closed with a door 11. The door is shown in closed position in FIGS. 1 and 2, and in open position in FIGS. 3 and 4. The opening 10 has dimensions that are appropriate for the active part 4 of the probe 2 to pass through. The door 11 is opened so that the active part 4 of a probe 2 can be placed in the decontamination space 9, and then it is closed for disinfection. When the door 11 is closed, the space 9 is hermetically closed so as to keep the disinfectant active principle from leaking out of the enclosure 3.

Figure 3:
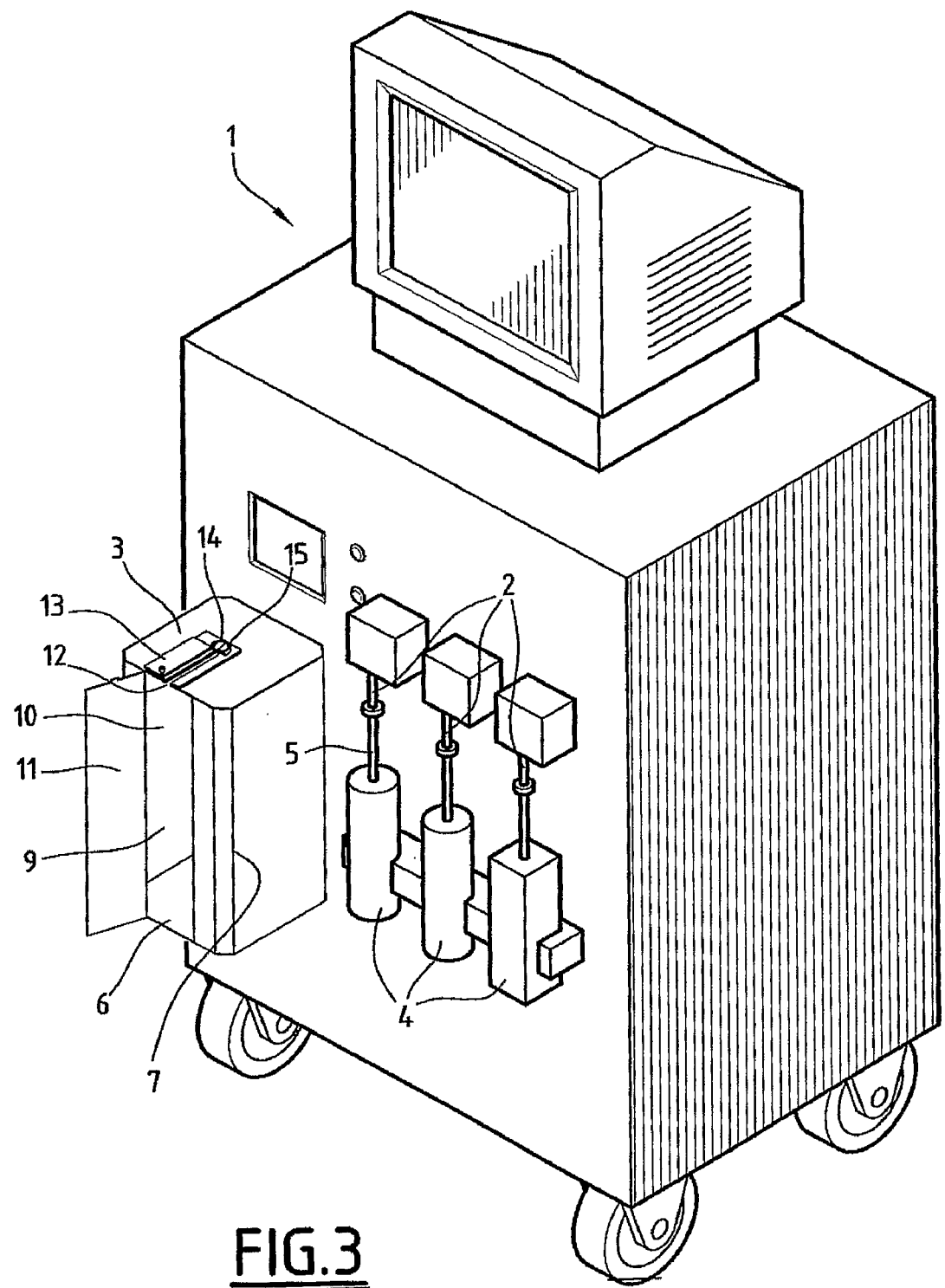
FIG. 3 is a schematic perspective view of the medical imaging device in FIG. 1, with the enclosure open.
Figure 4:
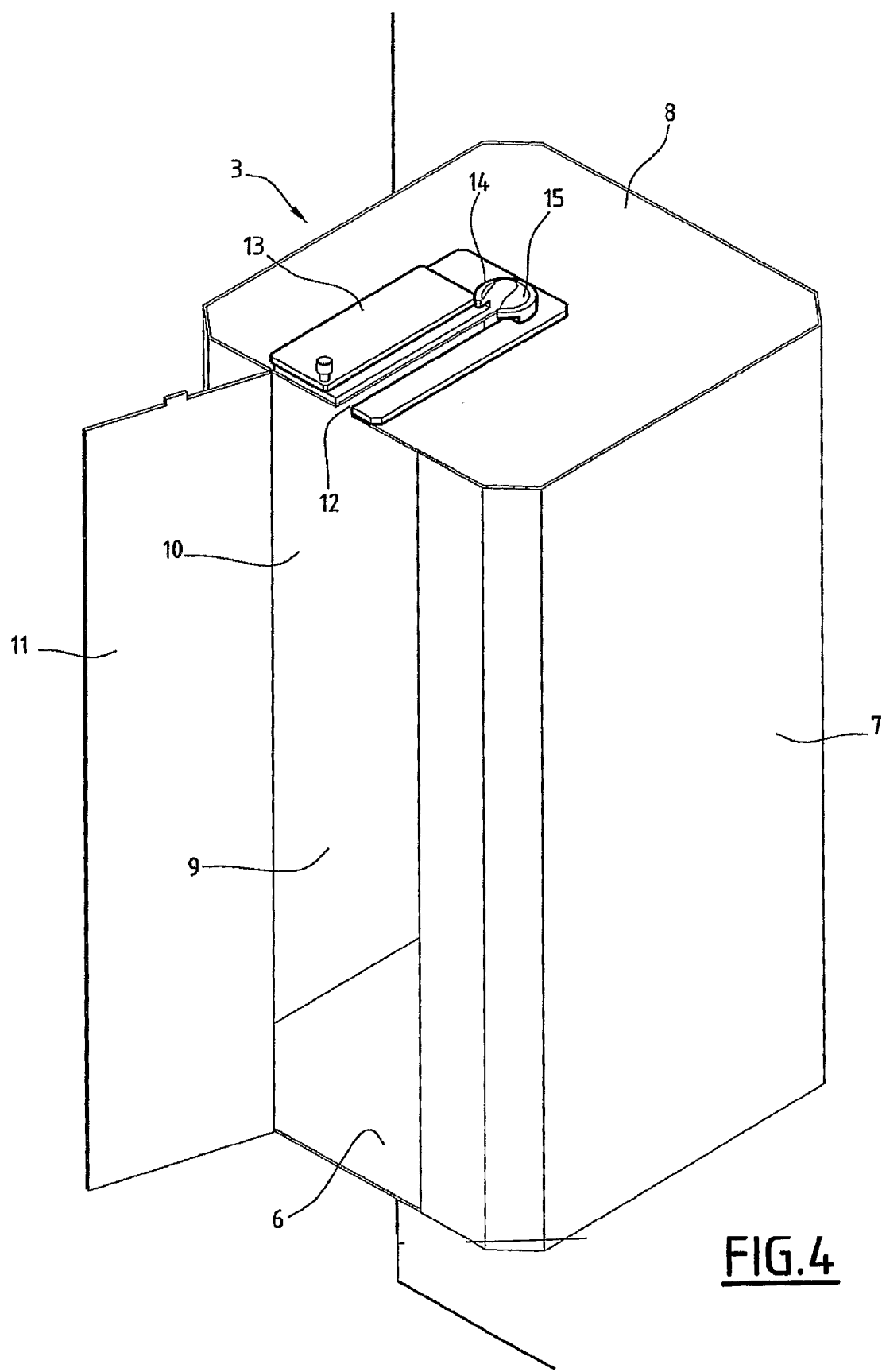
FIG. 4 is a schematic perspective view of the open enclosure in FIG. 3.

The cover 8 comprises a cable passage 12 that opens into the opening 10 so that the probe 2 cable 5 can pass through when the active part 4 is inserted into the decontamination space 9. The cable passage 12 comprises a slot provided in the cover 8, extending to a central part of the cover 8, as shown in FIGS. 3 and 4.

According to an embodiment shown in the figures, the cover 8 additionally comprises a flap seal 13 that is movable between a closed position (FIGS. 1 and 2) of the cable passage 12 and an open position (FIGS. 3 and 4) of the cable passage 12. The flap 13 closes the cable passage 12 hermetically when it is in the closed position. This way, when the active part 4 of the probe 2 has been inserted into the decontamination space 9, the door 11 and the flap 13 are put in the closed position so as to hermetically isolate the space 9 from the outside of the enclosure, and allow the active part 4 to be safely disinfected. According to an embodiment, the door 11 is arranged so that when it closes, it brings the mobile flap 13 into the position where it closes off the cable passage 12. Thus, all the operator has to do is close the door 11 for the flap to be automatically placed in closed position, which prevents handling errors if the operator forgets to actuate the flap 13 after having placed the probe 2 in the enclosure 3.

According to another embodiment not shown, the flap 13 is integral with the top part of the door 11 and is arranged so as to close the cable passage 12 hermetically when the door is closed. Such an embodiment is particularly simple to implement and does not require any means for transmitting movement between the door 11 and the flap 13, unlike the case in which the flap 13 is borne by the cover 8.

Figure 2:
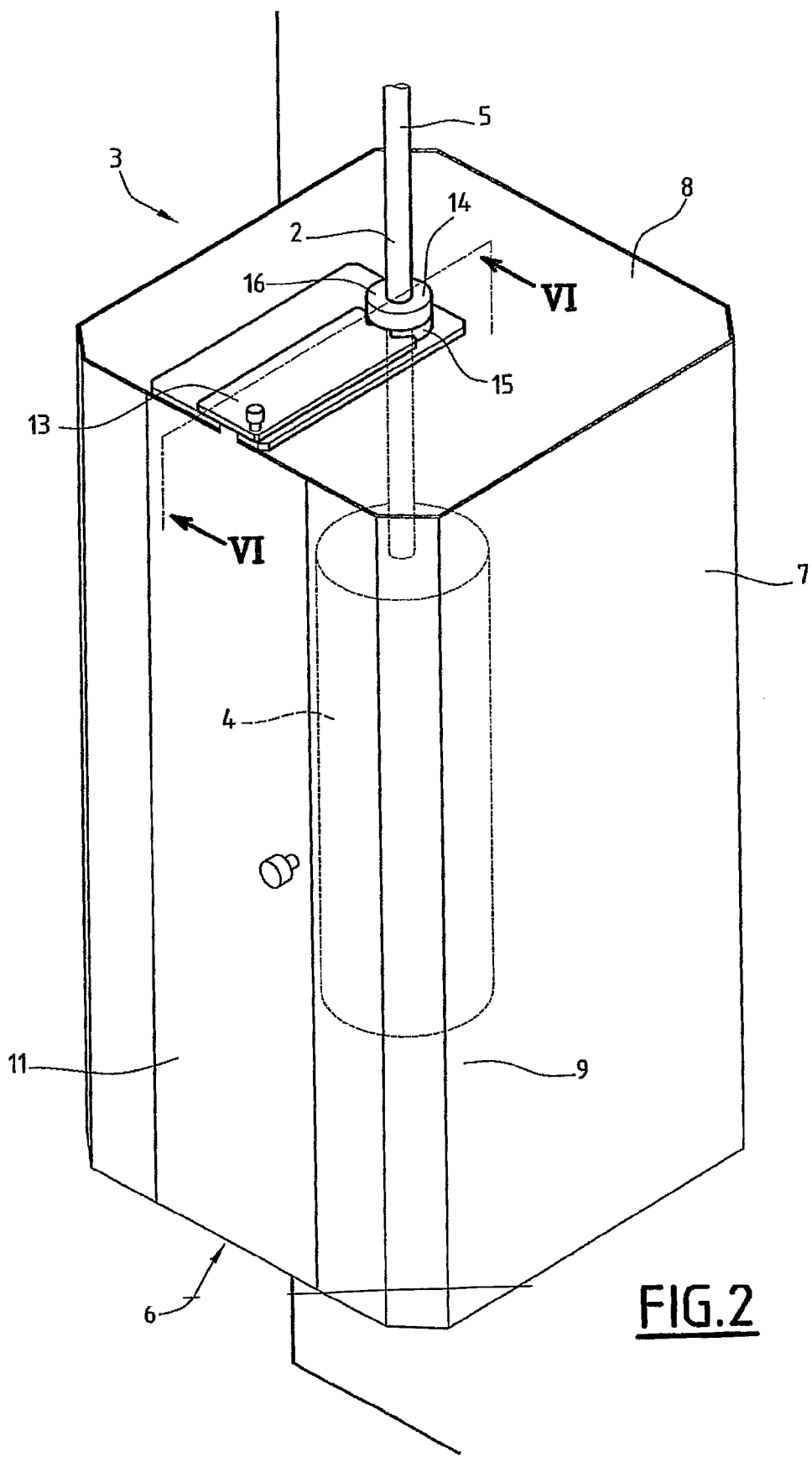
FIG. 2 is a schematic perspective view of the enclosure in FIG. 1, in which a probe has been placed.
Figure 6:
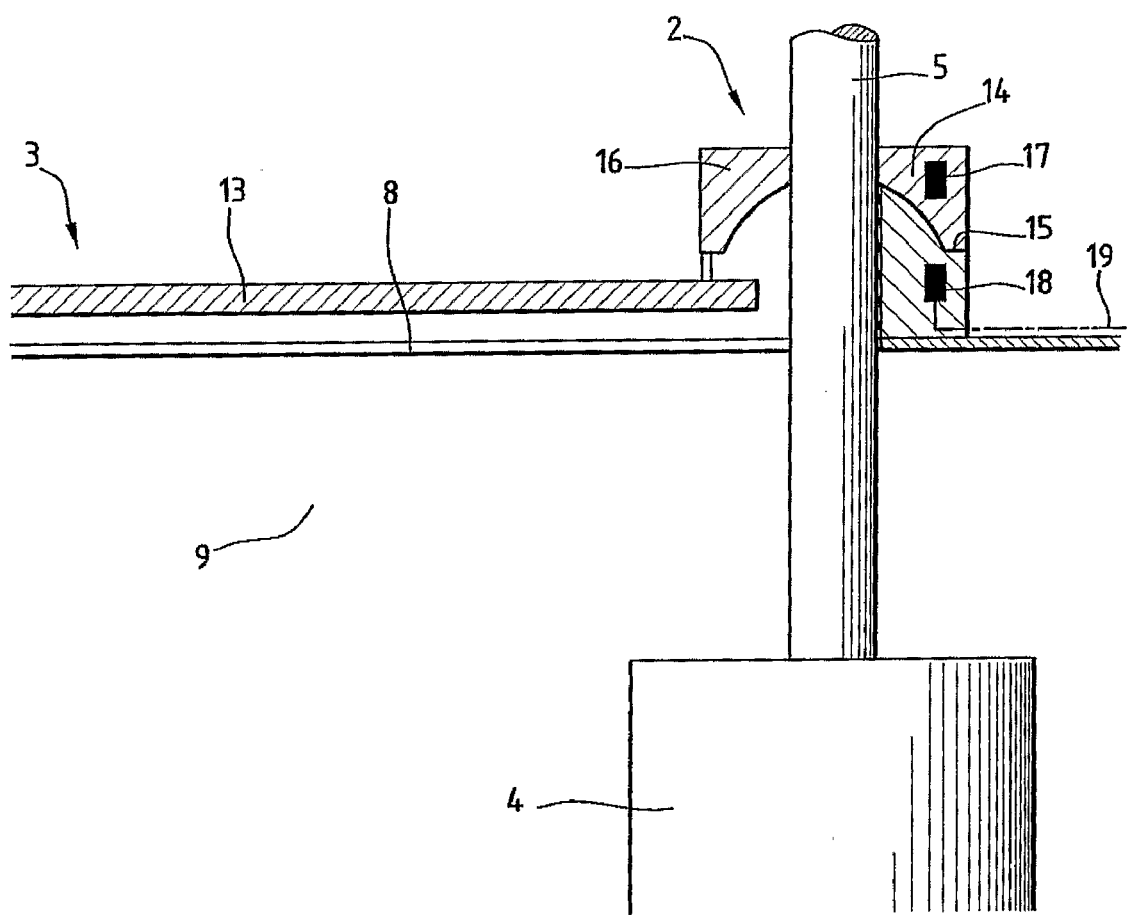
FIG. 6 is a schematic sectional view along the line VI-VI in FIG. 2.

The cover 8 additionally comprises a member 14 for suspending the cable through the cable passage 12. The cable suspension member 14 makes it possible to keep the probe 2 cable 5 in place so that the active part 4 is suspended in a substantially central part of the decontamination space 9, as shown in FIGS. 1, 2 and 6. The active part 4 is thereby prevented from touching the walls 7 of the enclosure 3, ensuring that the active part is uniformly exposed to the disinfectant active principle.

According to the embodiment shown in the figures, the suspension member 14 comprises a part 15 for receiving a suspension part 16 provided on the probe 2 cable 5. The receiving part 15 and the suspension part 16 form a fastening assembly comprised of a male part and a female part. According to the embodiment shown in the figures, the male part is the receiving part 15 and the female part is the suspension part 16.

According to an embodiment, the fastening assembly is arranged so that the cable 5 is oriented in a particular way when the suspension part 16 is attached onto the receiving part 15. For example, the cable is oriented by screwing the suspension part 16 onto the receiving part 15 until an abutting position is reached.

As shown in FIG. 6, the flap 13 and the fastening assembly are arranged so that the enclosure 3 is hermetically closed when the suspension part 16 is attached onto the receiving part 15 and the flap 13 is closed.

According to other embodiments not shown, the suspension member 14 comprises a clamp, a hook, or an open tube that can be hermetically fitted over a portion of cable 5 whose diameter is within a range of predetermined diameters. According to various embodiments, means are provided for orienting the cable 5, e.g., by indexing or other means, so that the cable has a predetermined orientation when the active part 4 is suspended in the decontamination space 9.

Figure 5:
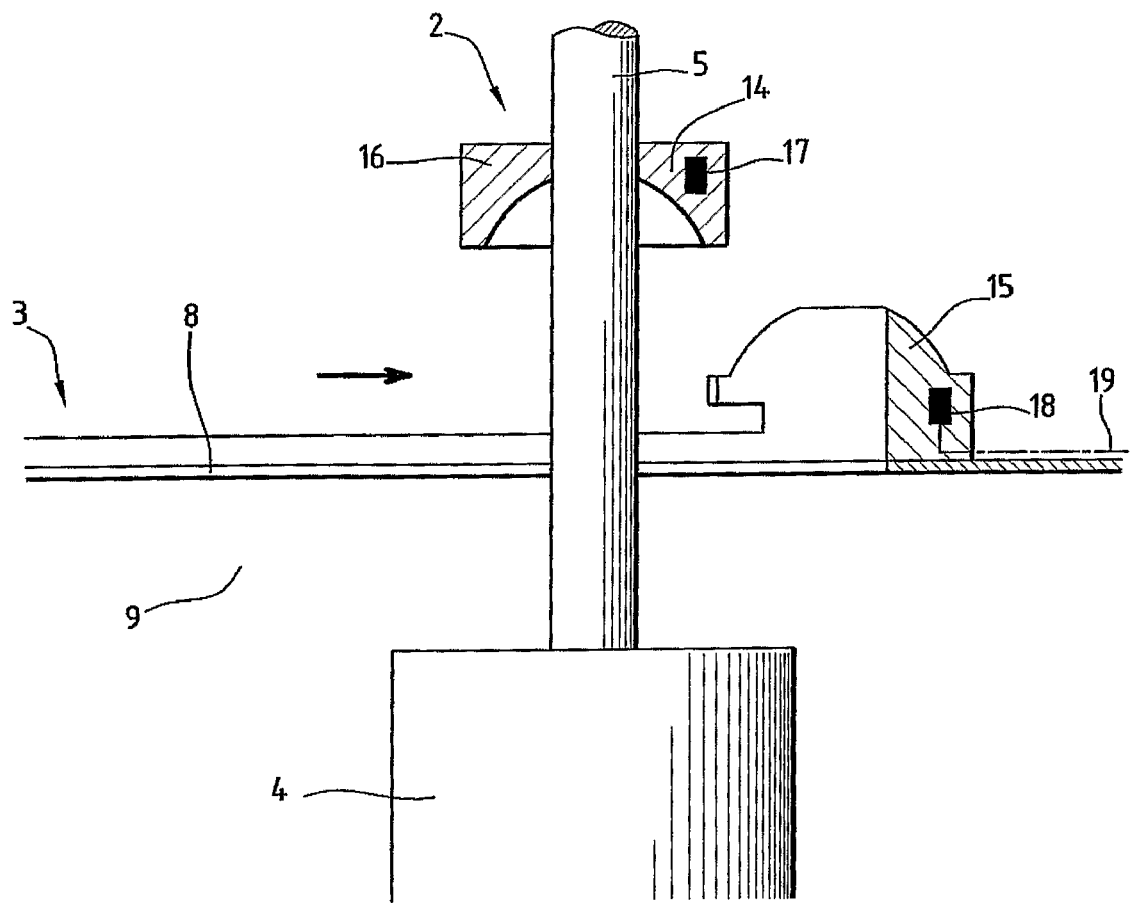
FIG. 5 is a schematic sectional view of the fastening assembly of the probe cable and of the enclosure, in the process of being put together.

In order to make the disinfection of a probe traceable so as to prevent any wrongful use of a probe from a hygienic standpoint, it is important to be able to accurately identify the probe that is being disinfected in the enclosure. To this end, according to an embodiment, the probe 2 comprises identification means in the form of an electronic identification label 17, e.g., an RFID chip. This chip contains information on the identity of the probe. The label 17 is attached to the cable 5, for example, near the suspension member 14 when the active part 4 of the probe 2 is suspended in the decontamination space 9. According to an embodiment, the label 17 is attached or embedded in the suspension part 16, as shown in FIGS. 5 and 6.

The enclosure comprises means 18 for reading the electronic identification label, e.g., an RFID-type reader. The reading means 18 are arranged so as to be near the identification label 17 when the cable 5 is suspended on the cable suspension member 15, so that the reading means 18 can read the identification information in the identification label 17. Placing the reading means near the identification label can be made simpler by the cable 5 orientation means. According to an embodiment, the reading means 18 are provided with the suspension member 15 or integrated therein, as shown in FIGS. 5 and 6. The reading means 18 are a short-range RFID reader, for example. This way, the reader can read only the information contained in the identification label attached to the cable 5 of the probe 2 suspended in the enclosure 3, and not the information for nearby probes, such as the other probes shown in FIG. 1. The reading means 18 are connected to the imaging device 1 or to a data processing system, e.g., via a wire connection 19. According to another embodiment, the reading means are connected via a wireless connection.

According to another embodiment not shown, the electronic identification label 17 is attached on the inside of a projection of the cable 5, which is inserted into the cable passage 12. The cable passage 12 comprises a recess to accommodate the projection, near which the reading means 18 are placed. A recess is provided, for example, at the end of the slot provided in the cover 8, into which the projection fits when the cable 5 is suspended in the enclosure. The reading means 18 near the recess make it possible to read the content of the identification label 17 attached inside the projection. The protrusion is arranged to fit into the recess in such a way that the enclosure 9 is hermetically closed when the active part 4 of the probe is inserted into the enclosure.

The identification label 17 of the probe 2 can operate in tandem with means (not shown) for measuring disinfection characteristics in order to make the disinfection of the probe traceable. For example, means can be provided for measuring the intensity of the UV radiation and the length of time the active part 4 is exposed to this radiation, if UV disinfection is used. This information can be recorded in the identification label of the probe or in the imaging device 1 with the identity of the probe 2. In this way, the probe identification information is paired with the disinfection information for this probe so as to make the disinfection process traceable.

According to an embodiment, the imaging device 1 is set up so that it will not operate with a probe that has not been disinfected or has been inadequately disinfected.

The invention claimed is:

1. Decontamination enclosure for medical instruments, comprising a base, at least one side wall, and a top cover, which delimit a decontamination space, wherein one of said at least one side walls comprises an opening extending to the top cover for access to the decontamination space, and the top cover comprises a cable passage that opens into said opening and a member for suspending a cable through said cable passage, said enclosure further comprising a flap seal that is movable between a closed position of the cable passage, in which the flap closes the cable passage hermetically, and an open position of the cable passage.

2. Enclosure according to claim 1, wherein the cable passage comprises a slot provided in the top cover.

3. Enclosure according to claim 1, wherein the flap is borne by the cover.

4. Enclosure according to any of claim 1, which comprises a door for closing the access opening to the decontamination space, with said door arranged so that closing it brings the mobile flap toward a position where it closes off the cable passage.

5. Enclosure according to claim 4, wherein the flap is integral with the top part of the door and is arranged so as to close the cable passage hermetically when the door is closed.

6. Enclosure according to claim 1, wherein the cable suspension member comprises a clamp.

7. Enclosure according to claim 1, wherein the cable suspension member comprises a hook.

8. Enclosure according to claim 1, wherein the cable suspension member comprises an open tube that is hermetically fittable over a portion of the medical instrument cable, whose diameter is within a range of predetermined diameters.

9. Enclosure according to claim 1, wherein the suspension member comprises a part for receiving a suspension part provided on the cable of the medical instrument, wherein said receiving part and said suspension part form a fastening assembly comprised of a male part and a female part.

10. Enclosure according to claim 1, wherein the enclosure comprises means for reading an electronic identification label provided on a cable of the medical instrument, with said label being placed near the active part of the medical instrument to be disinfected, and said reading means being arranged so as to be near the identification label when the cable is suspended on the cable suspension member.

11. Enclosure according to claim 10, wherein the means for reading an electronic identification label comprise a short-range RFID reader.

* * * * *